(12) United States Patent
Machida et al.

(10) Patent No.: US 12,414,712 B2
(45) Date of Patent: Sep. 16, 2025

(54) INFORMATION PROCESSING SYSTEM

(71) Applicants: CONNECTEC JAPAN CORPORATION, Myoukou (JP); FUJIKIN INCORPORATED, Osaka (JP)

(72) Inventors: Hidekazu Machida, Myoukou (JP); Nozomi Shimoishizaka, Myoukou (JP); Hiroshi Komatsu, Myoukou (JP)

(73) Assignees: CONNECTEC JAPAN Corporation, Niigata (JP); FUJIKIN INCORPORATED, Osaka (JP)

( * ) Notice: Subject to any disclaimer, the term of this patent is extended or adjusted under 35 U.S.C. 154(b) by 523 days.

(21) Appl. No.: 16/772,652

(22) PCT Filed: Dec. 6, 2018

(86) PCT No.: PCT/JP2018/044838
§ 371 (c)(1),
(2) Date: May 14, 2021

(87) PCT Pub. No.: WO2019/117002
PCT Pub. Date: Jun. 20, 2019

(65) Prior Publication Data
US 2021/0278925 A1    Sep. 9, 2021

(30) Foreign Application Priority Data
Dec. 12, 2017   (JP) .................. 2017-238177

(51) Int. Cl.
*G06F 3/041* (2006.01)
*A61B 5/1171* (2016.01)
(Continued)

(52) U.S. Cl.
CPC .......... *A61B 5/1171* (2016.02); *G06F 3/0412* (2013.01); *G06F 3/0425* (2013.01);
(Continued)

(58) Field of Classification Search
None
See application file for complete search history.

(56) References Cited

U.S. PATENT DOCUMENTS

| | | |
|---|---|---|
| 2009/0102788 A1 | 4/2009 | Nishida et al. |
| 2012/0223916 A1* | 9/2012 | Kukulj .................. G06F 3/0428 178/18.09 |

(Continued)

FOREIGN PATENT DOCUMENTS

| | | |
|---|---|---|
| CN | 106233295 A | 12/2016 |
| EP | 3168782 A1 | 5/2017 |

(Continued)

OTHER PUBLICATIONS

English machine translation of Japanese patent publication JP2007293539 (Year: 2007).*

(Continued)

*Primary Examiner* — Nicholas J Lee
(74) *Attorney, Agent, or Firm* — Maine Cernota & Curran

(57) ABSTRACT

A technique is provided that is capable of obtaining image data for personal identification clearly in a short time at an arbitrary position in an area region at least about several times greater than a fingertip. In addition, a technique is provided that allows smooth progress of a series of process flow in a reservation site and an electronic commerce site for excellent user experience. An information processing system is provided that includes: an input section having a surface and configured to allow a user to contact or approximate a position specifier to the surface for information input; and a processing section configured to perform processing based on the information input to the input section, wherein the input section includes a position detection mechanism configured to detect a position of the position specifier on the (Continued)

surface and a reading mechanism configured to read biometric information of the user.

8 Claims, 13 Drawing Sheets

(51) Int. Cl.
    *G06F 3/042*     (2006.01)
    *G06F 21/32*     (2013.01)
    *G06V 40/10*     (2022.01)
    *G06V 40/13*     (2022.01)
    *G06V 40/70*     (2022.01)

(52) U.S. Cl.
    CPC .............. *G06F 21/32* (2013.01); *G06V 40/13* (2022.01); *G06V 40/70* (2022.01); *G06V 40/15* (2022.01)

(56) References Cited

U.S. PATENT DOCUMENTS

| | | | |
|---|---|---|---|
| 2016/0092018 A1* | 3/2016 | Lee | G06F 1/1684 345/173 |
| 2016/0349882 A1 | 12/2016 | Liu et al. | |
| 2017/0220838 A1 | 8/2017 | He et al. | |
| 2018/0157395 A1* | 6/2018 | Mhun | G06F 3/04883 |
| 2019/0095672 A1* | 3/2019 | Yeke Yazdandoost | H01L 27/14685 |

FOREIGN PATENT DOCUMENTS

| | | |
|---|---|---|
| JP | 2004-39909 A | 2/2004 |
| JP | 2004-178166 A | 6/2004 |
| JP | 2004-334788 A | 11/2004 |
| JP | 2006-92428 A | 4/2006 |
| JP | 2007-293539 A | 11/2007 |
| JP | 2016-212843 A | 12/2016 |
| JP | 2017-33499 A | 2/2017 |
| JP | 2013-511100 A | 3/2018 |
| KR | 10-2010-0038157 A | 4/2010 |
| KR | 10-2016-0003272 A | 1/2016 |
| WO | 2011/060487 A1 | 5/2011 |
| WO | 2017/110218 A1 | 6/2017 |

OTHER PUBLICATIONS

English machine translation of Japanese patent publication JP2006092428 (Year: 2006).*
English machine translation of WIPO patent publication WO2017110218 (Year: 2017).*
International Search Report and Written Opinion, International Patent Application No. PCT/JP2018/044838, Mar. 5, 2018, with English translation of Search Report (10 pages).

* cited by examiner

INFORMATION PROCESSING SYSTEM

TECHNICAL FIELD

The present invention relates to an information processing system.

BACKGROUND ART

PTL 1 discloses an imaging device to obtain an optical image of a subject, particularly to an imaging device suitable for obtaining a fingerprint image for personal identification. A fingerprint at a fingertip may have low ridges depending on a person, and in such a case, a fingerprint reader is sometimes not capable of obtaining fingerprint image data, or even when being capable of obtaining, the obtained data is sometimes not clear. The imaging device in PTL 1, however, is supposed to achieve an object of the invention to "allow clear imaging of a subject" by providing a configuration of "an imaging device, configured to obtain an optical image of a subject (e.g., a fingertip) from below a contact surface that contacts the subject, wherein a light diffusing film to diffuse light is formed on the contact surface".

PTL 2 discloses a contact sensor to sense a test object. Similar to the case of PTL 1 above, a fingerprint reader is sometimes not capable of obtaining fingerprint image data, or even when being capable of obtaining, the obtained data is sometimes not clear. The contact sensor in PTL 2, however, is supposed to achieve an object of the invention to "allow clear imaging of a subject" by providing a configuration of "a contact sensor, configured to sense a test object placed on a placement surface, wherein a liquid repellent coating is formed on the placement surface".

In sites to reserve tickets for hotels, flights, and the like and electronic commerce sites for purchase of goods and the like, personal identification is generally required for, in addition to login to start providing the service, an important procedure such as a payment procedure during a series of process of reservation or purchase of goods.

CITATION LIST

Patent Literature

PTL 1: JP 2004-39909 A
PTL 2: JP 2004-178166 A

SUMMARY OF INVENTION

Technical Problem

Use of the techniques described in PTLs 1 and 2 allows clear fingerprint image data to be obtained for personal identification.

However, the inventions described in PTLs 1 and 2 assume obtaining fingerprint image data in a limited area region of about a fingertip, for example a region of approximately 10 mm×10 mm, and thus to obtain clear fingerprint image data at an arbitrary position in a large area region of, for example, 10 inches or more, the number of scanning lines for data detection becomes enormous and it is difficult to quickly obtain image data.

For example, to obtain fingerprint image data with a resolution equivalent to PTLs 1 and 2, read sensors have to be arranged in an array with a 50 μm pitch, and the number of drivers for horizontal and vertical scanning is 5940×4200 for A4 size and 8400×5940 for A3 size. Such a large number of drivers has to be driven to read a fingerprint one time, causing a problem that the time taken to obtain the entire data becomes longer. Moreover, not all the data thus obtained is used for personal identification and the data used for personal identification is limited to the data in the region toughed by the fingertip and thus a large amount of data in the other regions turns out to be useless data not used for personal identification.

It is an object of the present invention to provide a technique capable of obtaining image data for personal identification clearly in a short time at an arbitrary position in an area region about several times greater than a fingertip.

It is another object of the present invention to provide a technique capable of obtaining image data for personal identification efficiently with no waste in an area region about several times greater than a fingertip.

As described above, reservation sites or electronic commerce sites may require personal identification every time a user selects a process of an important procedure, such as payment processing. The security of transactions is thus ensured by requiring personal identification every time processing an important procedure.

However, it is not convenient for the user required to provide personal identification for each important procedure due to interruption of a series of process flow for reservation or shopping. In addition, shopping in electronic commerce is, no different from shopping in a real store, to enjoy shopping and thus process interruption in a series of procedures by personal identification is not preferred from the perspective of user experience.

It is thus still another object of the present invention to provide a technique capable of smooth progress of a series of process flow in a reservation site or an electronic commerce site for excellent user experience.

Solution to Problem

To achieve the above problems, a first aspect of the present invention provides an information processing system, including: an input section having a surface and configured to allow a user to contact or approximate a position specifier to the surface for information input; and a processing section configured to perform processing based on the information input to the input section, wherein the input section includes a position detection mechanism configured to detect a position of the position specifier on the surface and a reading mechanism configured to read biometric information of the user.

The above information processing system may have a configuration in which the processing section narrows down a region to be read by the reading mechanism based on position information of the position specifier obtained from the position detection mechanism and activates the reading mechanism in the reading region to obtain the biometric information.

The above information processing system may have another configuration in which the processing section configured to perform next processing based on position information of the position specifier obtained from the position detection mechanism and attribute information of the user associated with the biometric information obtained from the reading mechanism. In this case, the above information processing system may further include a display section 210 arranged facing the input section, wherein the processing section selects and performs, in the next processing, a function in accordance with the attribute information among functions assigned to the position of the display section 210 specified in the position information.

The above information processing system may have a configuration in which the position detection mechanism is a device configured to cause the reading mechanism to function with reduced reading accuracy, a touch screen, or a single or a plurality of imaging devices. In this case, the above information processing system may have a configuration in which the reading mechanism has detection elements arranged in a matrix on the surface, first lines connecting the detection elements in a first direction, and second lines connecting the detection elements in a second direction different from the first direction and is configured to cause the reading mechanism to function as the position detection mechanism by reducing the first lines, the second lines, or both the first lines and the second lines during their function. The above information processing system may have another configuration in which the position detection mechanism is the plurality of imaging devices, and each of the imaging devices takes an image of a region different from each other on the surface.

The above information processing system may have a configuration in which the biometric information is a pattern or a feature corresponding to a single or a plurality of biometric areas selected from a fingerprint, a vein pattern, face, an iris, and a voiceprint of the user.

It should be noted that the summary of the invention described above does not list all characteristics necessary for the present invention. In addition, subcombinations of the groups of characteristics may also be the invention.

DESCRIPTION OF EMBODIMENTS

The present invention is described below with reference to embodiments while the following embodiments do not limit the invention defined in the appended claims. Not all combinations of the characteristics described in the following embodiments are essential to the solutions of the invention.

First Embodiment

Figure 1:
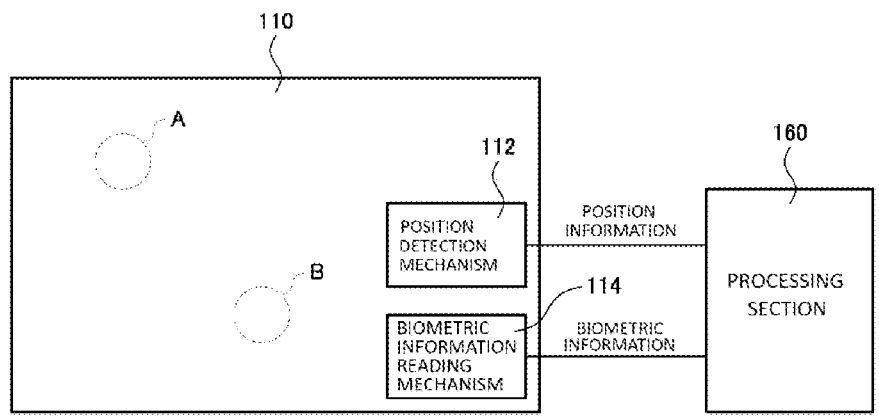
FIG. 1 is a conceptual diagram illustrating an information processing system 100.

FIG. 1 is a conceptual diagram illustrating an information processing system 100. The information processing system 100 has an input section 110 and a processing section 160, and the input section 110 has a position detection mechanism 112 and a biometric information reading mechanism 114.

The input section 110 has a surface and allows a user to contact or approximate a position specifier, such as a finger, to the surface for information input. The position detection mechanism 112 detects the position of the position specifier on the surface, and the biometric information reading mechanism 114 reads biometric information of the user. The processing section 160 performs processing based on the information input to the input section 110.

For example, when the user approximates or contacts, for example, a finger (position specifier) to a region A, the position detection mechanism 112 detects the region A and transmits the position information of the detected region A to the processing section 160. The biometric information reading mechanism 114 reads the biometric information from the body of the user, such as the fingerprint of the finger approximated or contacted to the region A and transmits the biometric information thus read to the processing section 160. When the user approximates or contacts a finger to a region B, the position information of the region B is transmitted to the processing section 160, and at the same time, the biometric information of the user is transmitted to the processing section 160.

Figure 2:
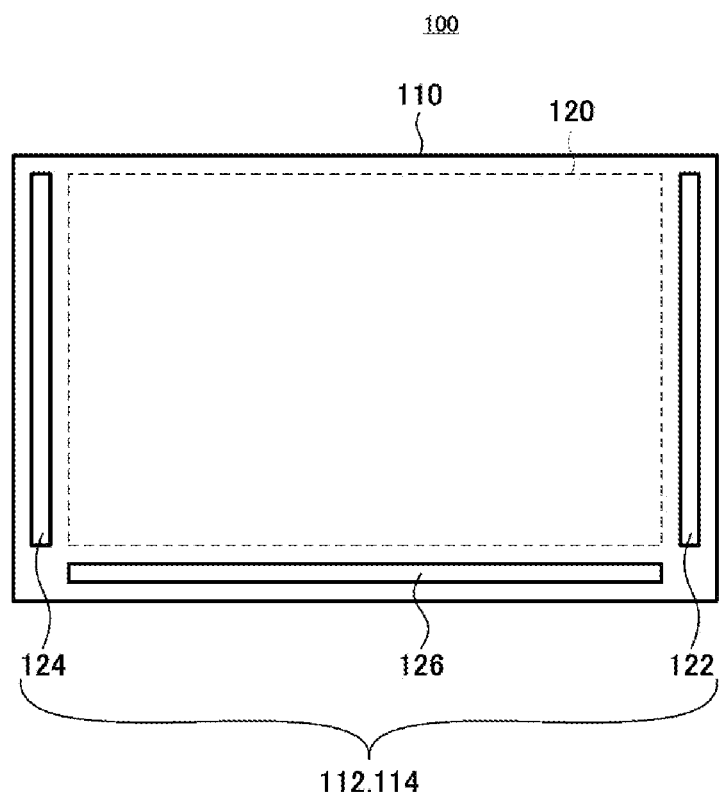
FIG. 2 is a diagram illustrating an example of an input section 110.
Figure 3:
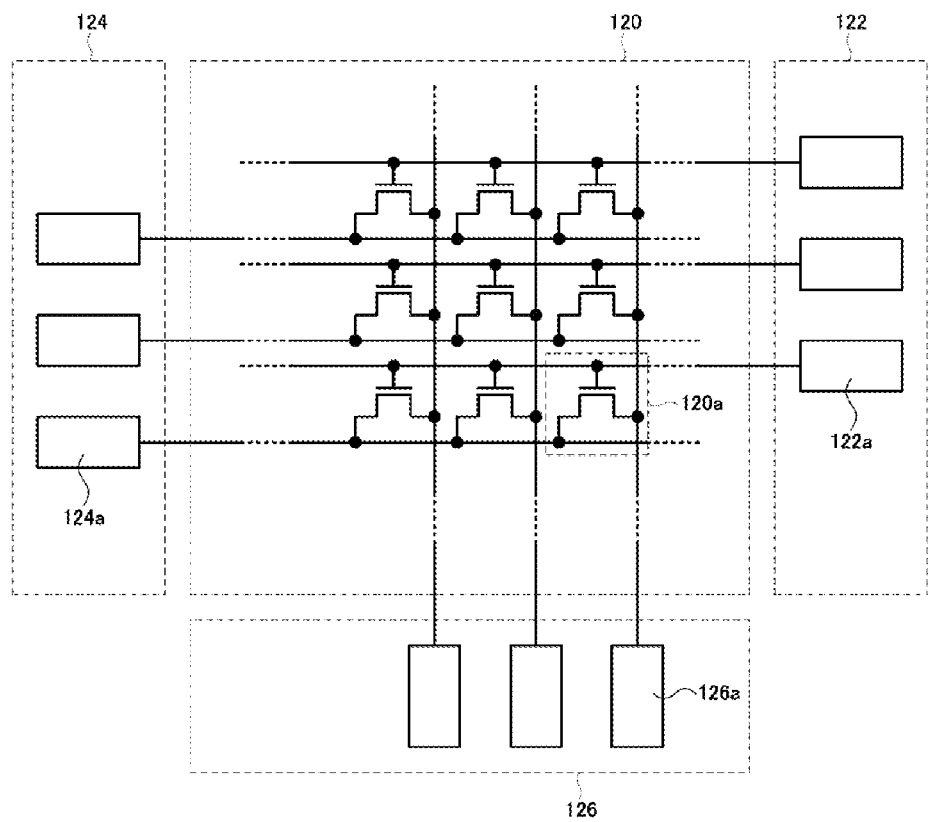
FIG. 3 is a partial enlarged view of the input section 110.

FIG. 2 is a diagram illustrating an example of the input section 110, and FIG. 3 is a partial enlarged view of the input section 110. The input section 110 illustrated in FIGS. 2 and 3 is illustrated as an example of the position detection mechanism 112 and the biometric information reading mechanism 114, where the position detection mechanism 112 is exemplified by a device causing the biometric information reading mechanism 114 to function with reduced reading accuracy.

The input section 110 has a detection element formation region 120, vertical driver formation regions 122 and 124, and a signal readout circuit formation region 126, where the vertical driver formation regions 122 and 124 are arranged respectively to the right and left of the detection element formation region 120 and the signal readout circuit formation region 126 is arranged below the detection element formation region 120. It should be noted that the above expressions of the right and left and above and below merely express the directions in FIG. 2 and do not mean directions in an actual product.

In the detection element formation region 120, detection elements 120a, first lines 120b, and second lines 120c are formed. In the vertical driver formation regions 122 and 124, respective vertical drivers 122a and 124a are formed. In the signal readout circuit formation region 126, signal readout circuits 126a are formed.

The detection elements 120a are arranged in a matrix on a surface of the input section 110 and are exemplified by, for example, photosensitive thin-film transistors. To obtain fingerprint image data with a resolution for personal identification, the detection elements 120a are preferably arranged with a pitch of, for example, 50 µm approximately.

The first lines 120b connect the detection elements 120a in a first direction and the second lines 120c connect the detection elements 120a in a second direction different from the first direction. For example, as illustrated in FIG. 3, the first lines 120b connect gate electrodes of the detection elements 120a in a horizontal row to each other and are connected to the vertical drivers 122a. The first lines 120b also connect source electrodes (or drain electrodes) of the detection elements 120a in a horizontal row to each other and are connected to the vertical drivers 124a. The second lines 120c connect drain electrodes (or source electrodes) of the detection elements 120a in a vertical row to each other and are connected to the signal readout circuits 126a.

Figure 4:
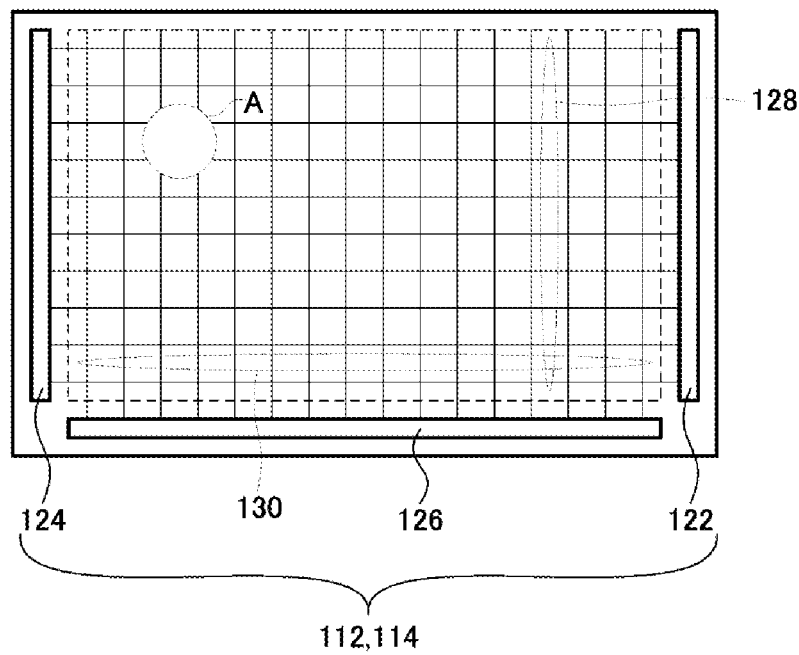
FIG. 4 is a diagram illustrating functions of the information processing system 100.
Figure 5:
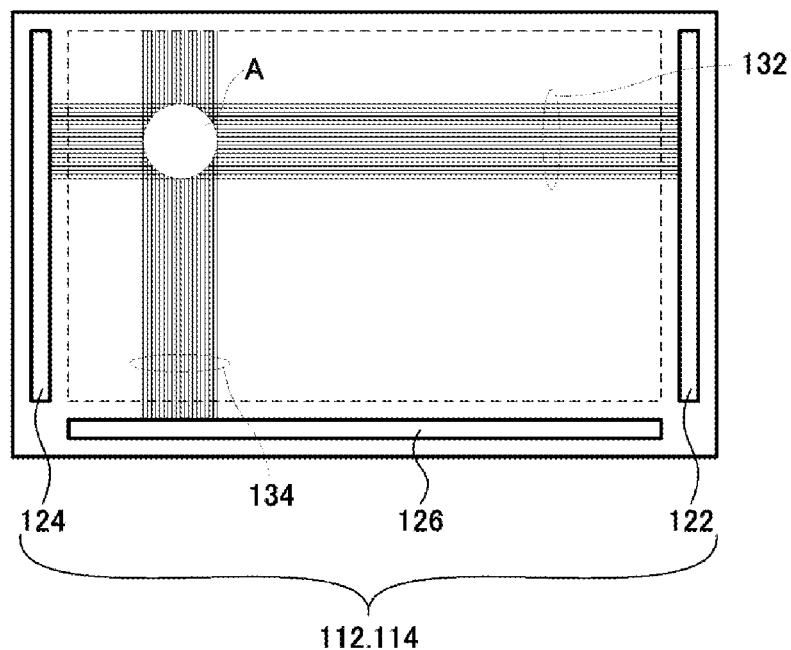
FIG. 5 is a diagram illustrating functions of the information processing system 100.

FIGS. 4 and 5 are diagrams illustrating functions of the information processing system 100. In the information processing system 100, the processing section 160 narrows down a region to be read by the biometric information reading mechanism 114 based on the position information of the position specifier obtained from the position detection mechanism 112 and activates the biometric information reading mechanism 114 in the reading region thus narrowed down to obtain the biometric information. That is, when a user contacts a finger as the position specifier to the region A, the processing section 160 causes the position detection mechanism 112 to specify the region A to narrow down the region to be read by the biometric information reading mechanism 114 to the region A and causes the biometric information reading mechanism 114 to be activated in the region A to obtain the biometric information.

For example, at the point when the processing section 160 obtains the position information of the position specifier (e.g., a finger of the user) by the position detection mechanism 112, as illustrated in FIG. 4, the detection elements 120a are activated only on horizontal coarse lines 128 prepared by reducing the first lines 120b and vertical coarse lines 130 prepared by reducing the second lines 120c to obtain the region A as the position information. Then, first lines 132 in the region A and second lines 134 in the region A are activated to obtain detailed fingerprint image data in the region A. That is, functioning the first lines 120b and the second lines 120c by reducing them allows the biometric information reading mechanism 114 to function as the position detection mechanism 112.

Functioning the first lines 120b and the second lines 120c by reducing them thus allows the biometric information reading mechanism 114 to function as the position detection mechanism 112 and detailed fingerprint image data to be obtained in the region narrowed down by the position detection mechanism 112 to obtain image data clearly in a short time with a resolution for personal identification at an arbitrary position in a large area region. In addition, the detailed image data for personal identification is obtained only in a recommended region, allowing image data for personal identification to be obtained efficiently with no waste.

In the above case, the detection elements 120a, the first lines 120b, and the second lines 120c formed in the detection element formation region 120, the vertical drivers 122a and 124a formed in the vertical driver formation regions 122 and 124, and the signal readout circuits 126a formed in the signal readout circuit formation region 126 form the biometric information reading mechanism 114 and some of them also form the position detection mechanism 112. The position detection mechanism 112 may be expressed as a mechanism configured to cause the biometric information reading mechanism 114 to function with reduced reading accuracy.

Although the example has been described that both the first lines 120b and the second lines 120c are reduced in the operation of the processing section 160, it should be noted that only either the first lines 120b or the second lines 120c may be reduced to function.

Figure 6:
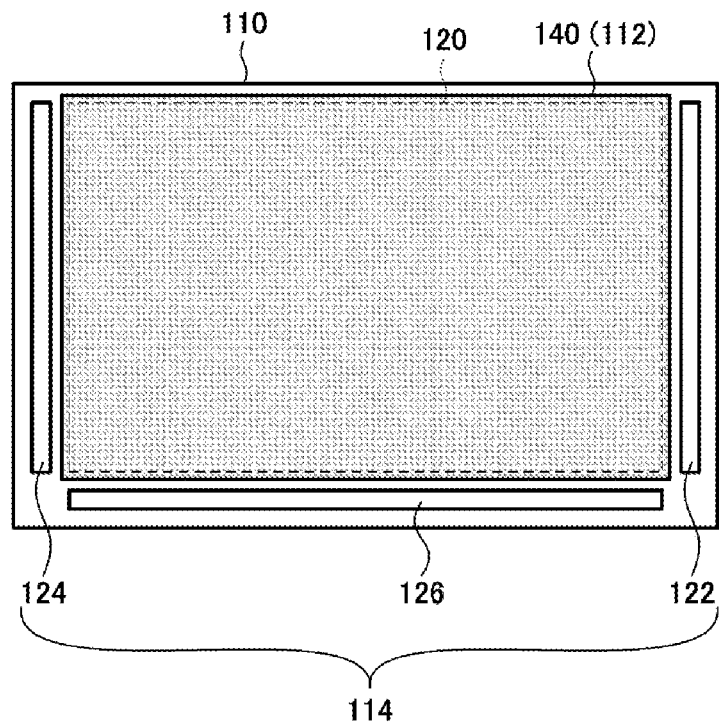
FIG. 6 is a diagram illustrating another example of the input section 110.

FIG. 6 is a diagram illustrating another example of the input section 110. The input section 110 illustrated in FIG. 6 has a touch screen 140 as the position detection mechanism 112. The touch screen 140 allows detection of the position of the position specifier, such as a finger of the user, and reading of the biometric information by narrowing down to the position. In this case, the detection elements 120a, the first lines 120b, and the second lines 120c formed in the detection element formation region 120, the vertical drivers 122a and 124a formed in the vertical driver formation regions 122 and 124, and the signal readout circuits 126a formed in the signal readout circuit formation region 126 form the biometric information reading mechanism 114.

Figure 7:
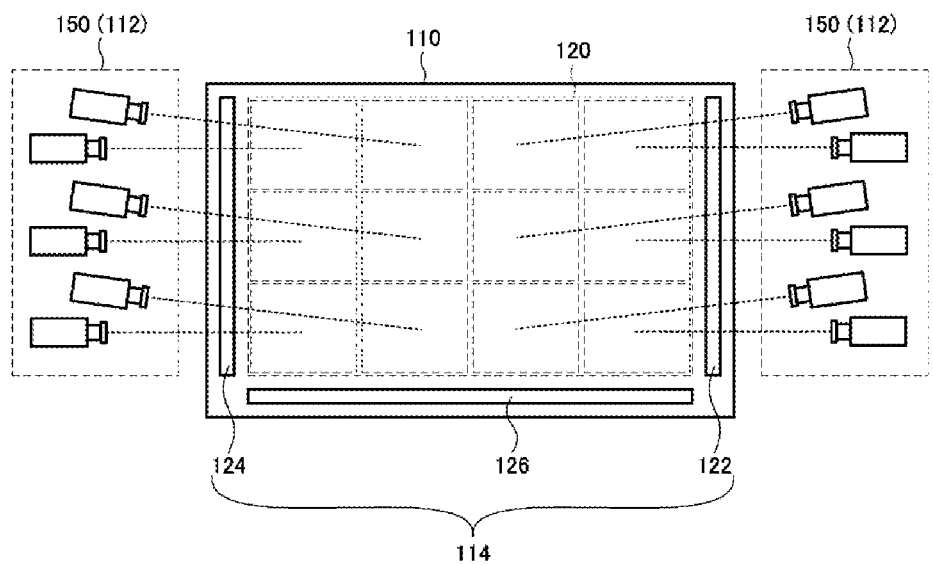
FIG. 7 is a diagram illustrating still another example of the input section 110.

FIG. 7 is a diagram illustrating still another example of the input section 110. The input section 110 illustrated in FIG. 7 has a plurality of imaging devices 150 as the position detection mechanism 112. Each imaging device 150 takes an image of a region 152 different from each other on the surface of the input section 110. Detecting in which region 152 corresponding to each imaging device 150 the position specifier, such as a finger of the user, is located allows detection of the position of the position specifier and reading of the biometric information by narrowing down to the position.

Although the detection elements 120a and the like formed in the detection element formation region 120 may be the biometric information reading mechanism 114, it should be noted that the image data taken by the imaging device 150 may be used as the fingerprint image data for obtaining the biometric information. In this case, the imaging device 150 also functions as the biometric information reading mechanism 114. When used as the biometric information reading mechanism 114, the imaging device 150 is preferably provided with a prism to contact a finger and the like. Although the case of the plurality of imaging devices 150 is described above as an example, a single imaging device 150 may be applied when the imaging device 150 is capable of covering the entire area of the input section 110 by adjusting the direction of imaging, the depth of focus, and the like.

Second Embodiment

Figure 8:
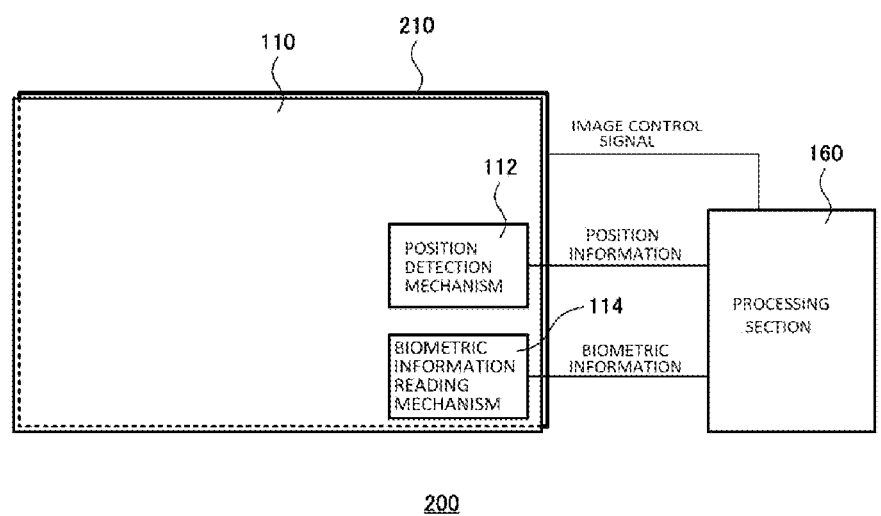
FIG. 8 is a conceptual diagram illustrating an information processing system 200.
Figure 9:
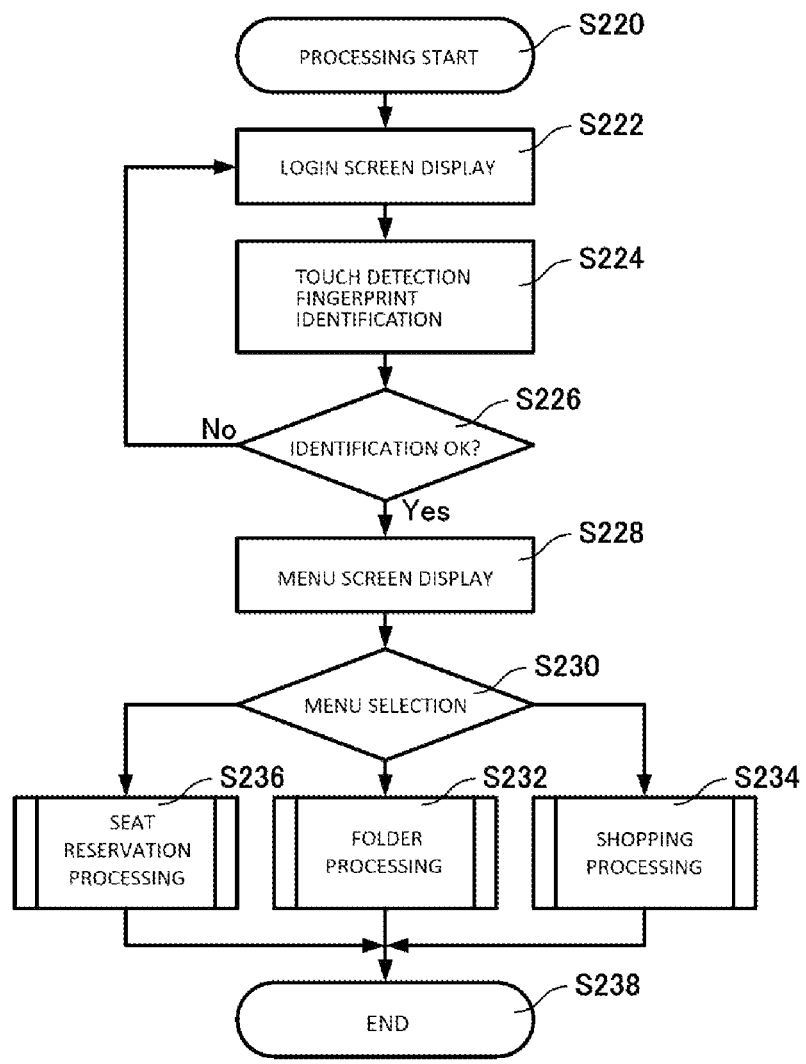
FIG. 9 is a flow chart illustrating processing of the information processing system 200.

FIG. 8 is a conceptual diagram illustrating an information processing system 200. The information processing system 200 has, in addition to a display section 210, the same configuration as the information processing system 100 in the first embodiment. The description on the same configuration as the information processing system 100 is omitted.

The display section 210 is a display device, such as a liquid crystal display device and an electroluminescent display device, and is arranged facing the input section 110. The input section 110 is transparent or semitransparent to allow a user to visually recognize the display contents of the display section 210 through the input section 110.

The processing section 160 is provided with, in addition to the functions described in the first embodiment, a function to control the display section 210. The processing section 160 performs next processing based on the position information of the position specifier obtained from the position detection mechanism 112 and the user attribute information, for example user identification information, associated with the biometric information obtained from the biometric information reading mechanism 114. For example, in the next processing, the processing section 160 selects and performs a function in accordance with the attribute information (e.g., payment processing in accordance with the user identification) among functions assigned to the position of the display section 210 specified in the position information (e.g., function of product selection in a shopping site and seat selection in a ticket reservation site). Specific examples are described below.

FIGS. 9, 12, 15, and 18 are flow charts illustrating processing of the information processing system 200. FIGS. 10, 11, 13, 14, 16, 17, 19, and 20 are diagrams illustrating examples of a display of the information processing system 200.

Figure 10:
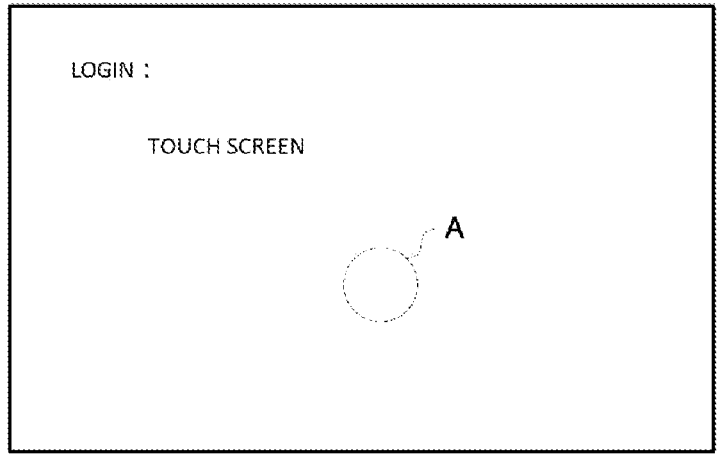
FIG. 10 is a diagram illustrating an example of a display of the information processing system 200.
Figure 11:
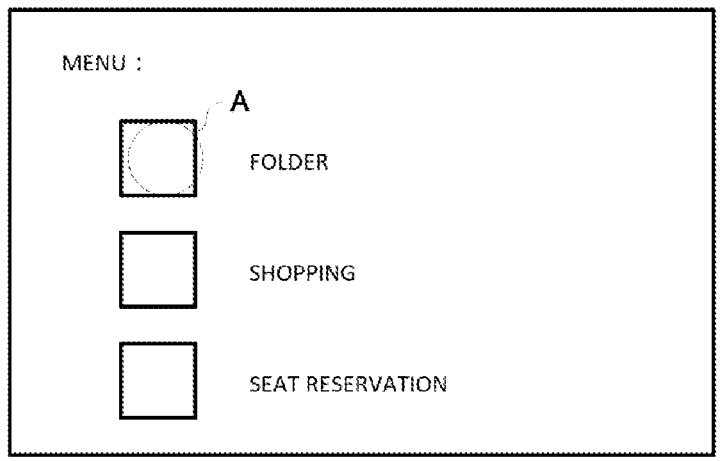
FIG. 11 is a diagram illustrating an example of a display of the information processing system 200.

In the information processing system 200, when the process is started (S220), a login screen is displayed as illustrated in FIG. 10 (S222), and for example, a user contacts a finger to the region A to perform touch detection and fingerprint identification (S224). When the user is identified by the fingerprint identification (S226), a menu screen as illustrated in FIG. 11 is displayed (S228). When not identified, the process goes back to the login screen at S222. On the menu screen in FIG. 11, menus of, for example, "Folder", "Shopping", and "Seat Reservation" are displayed and the process is branched to folder processing (S232), shopping processing (S234), and seat reservation processing (S236) in accordance with menu selection (S230) by the user. After performing the relevant processing, the process is terminated (S238).

The menu selection by the user is performed by, for example, contacting a finger of the user to any of the menu regions. For example, when the contacted region A is in a display region for the folder processing as illustrated in FIG. 11, the folder processing is selected.

Figure 12:
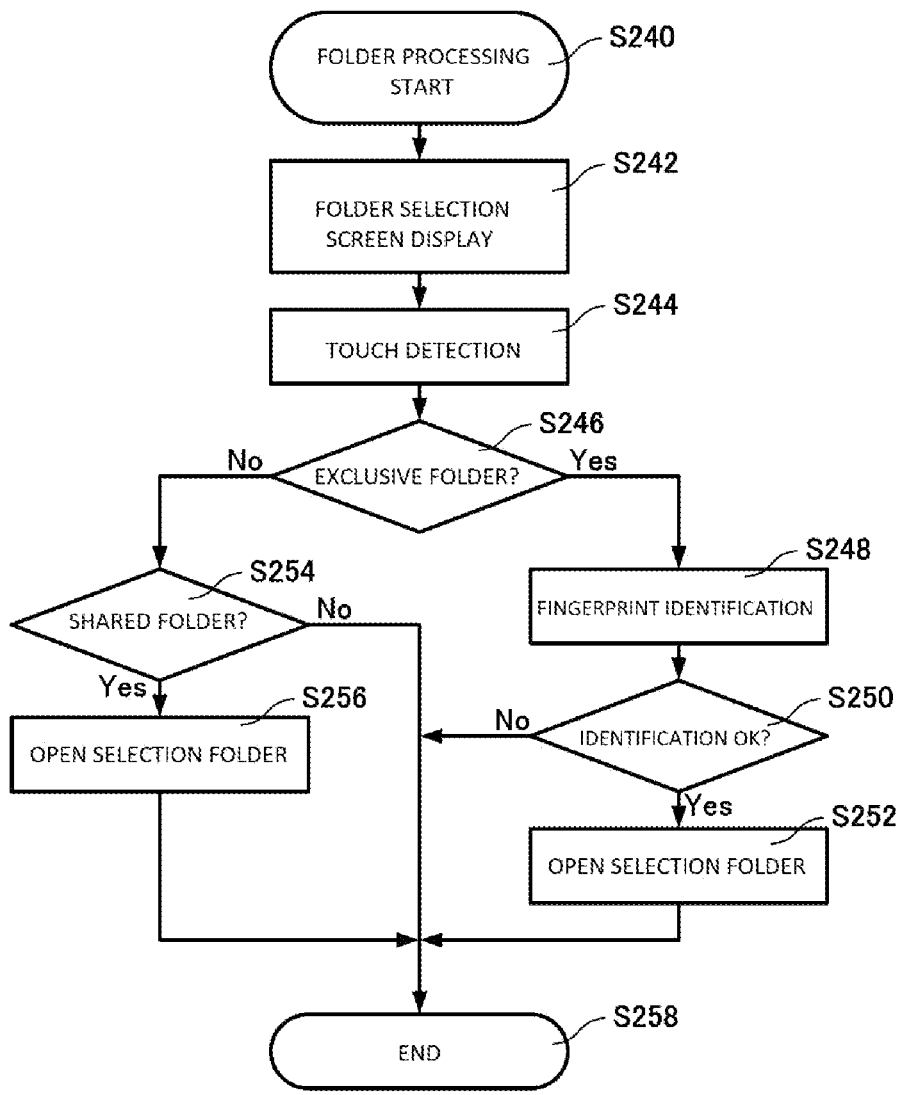
FIG. 12 is a flow chart illustrating processing of the information processing system 200.
Figure 13:
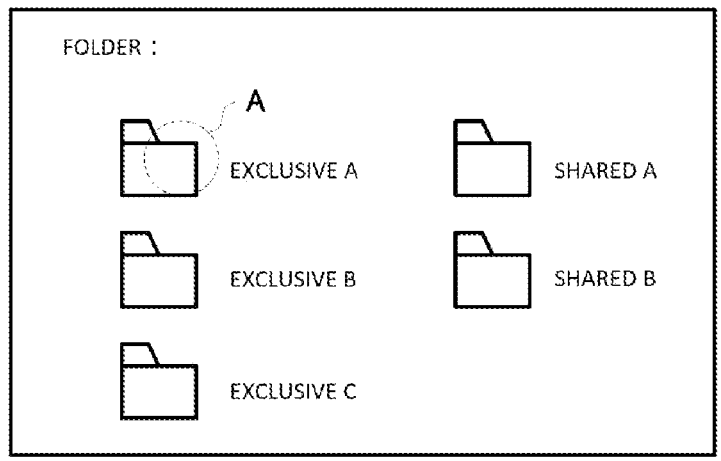
FIG. 13 is a diagram illustrating an example of a display of the information processing system 200.
Figure 14:
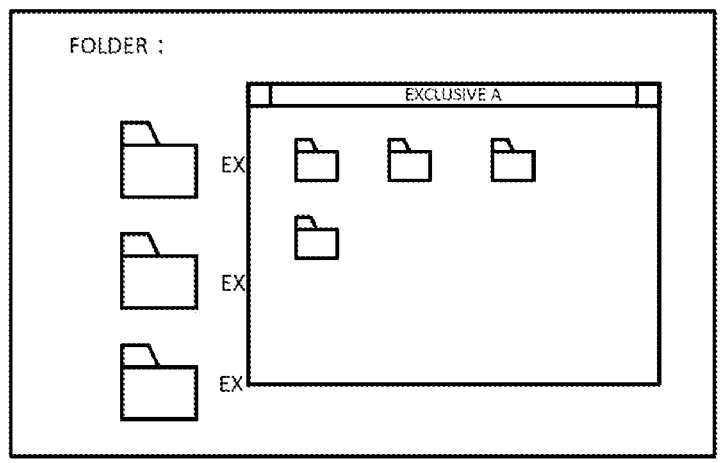
FIG. 14 is a diagram illustrating an example of a display of the information processing system 200.

FIG. 12 is an example of a process flow when the folder processing is selected. When the folder processing is started (S240), a folder selection screen is displayed (S242) as illustrated in FIG. 13 and touch detection is performed by, for example, contacting a finger to the region A by the user (S244). Whether the selected folder is a folder exclusive for the user is determined (S246), and when it is the exclusive folder, fingerprint identification is performed (S248). Whether the identification is passed in the fingerprint identification is determined (S250), and when the identification is passed, the selected exclusive A folder is opened (S252) as illustrated in FIG. 14. When the identification is not passed, the process is terminated (S258). When the selected folder is determined not as an exclusive folder at S246, whether it is a shared folder is determined (S254). A selection folder is then opened (S256) when it is a shared folder, while the process is terminated (S258) when it is not.

According to the flow in FIG. 12, one operation of contacting a finger (folder selection) by the user simultaneously allows selecting a folder and obtaining image data for passing the personal identification and thus allows the process to be performed without requesting data input and the like of the user for personal identification even when the selected folder is an exclusive folder. As a result, the process flow seen by the user is extremely smooth and it is thus possible to provide good user experience.

Figure 15:
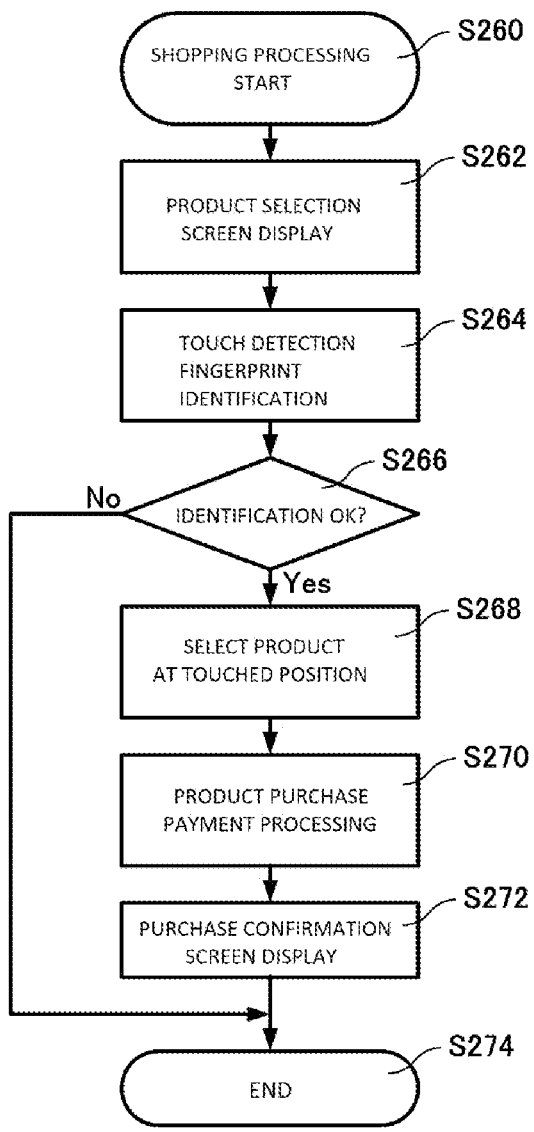
FIG. 15 is a flow chart illustrating processing of the information processing system 200.
Figure 16:
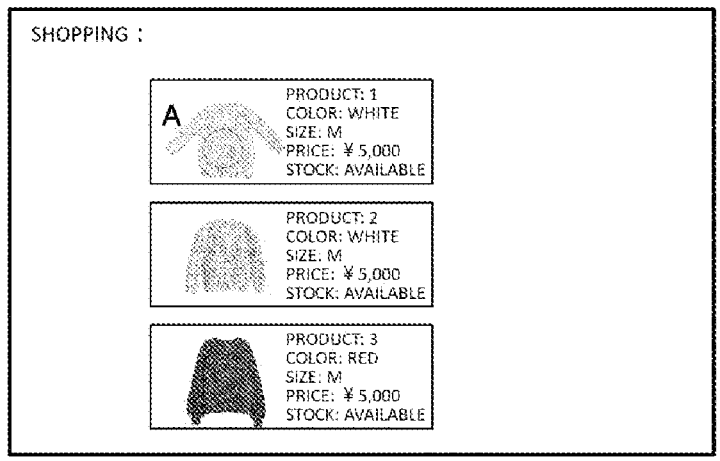
FIG. 16 is a diagram illustrating an example of a display of the information processing system 200.
Figure 17:
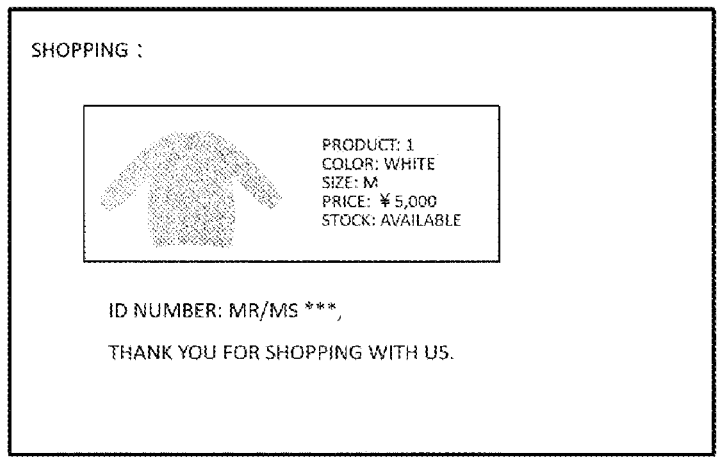
FIG. 17 is a diagram illustrating an example of a display of the information processing system 200.

FIG. 15 is an example of a process flow when the shopping processing is selected. When the shopping processing is started (S260), a product selection screen is displayed (S262) as illustrated in FIG. 16 and touch detection and fingerprint identification are performed by, for example, contacting a finger to the region A by the user (S264). Whether the identification is passed in the fingerprint identification is determined (S266), and when the identification is passed, a product at a touched position is selected (S268) and product purchase processing and payment processing are performed (S270). As illustrated in FIG. 17, a purchase confirmation screen is then displayed (S272) and the process is terminated (S274). When the identification is determined not to be passed at S266, the process is terminated (S274).

As just described, one operation of contacting a finger (product selection) by the user simultaneously allows selecting a product and obtaining image data for passing the personal identification and thus allows the process to be performed without requesting data input and the like of the user for user identification in the payment processing during the product purchase. As a result, the process flow seen by the user is extremely smooth and it is thus possible to provide good user experience.

Figure 18:
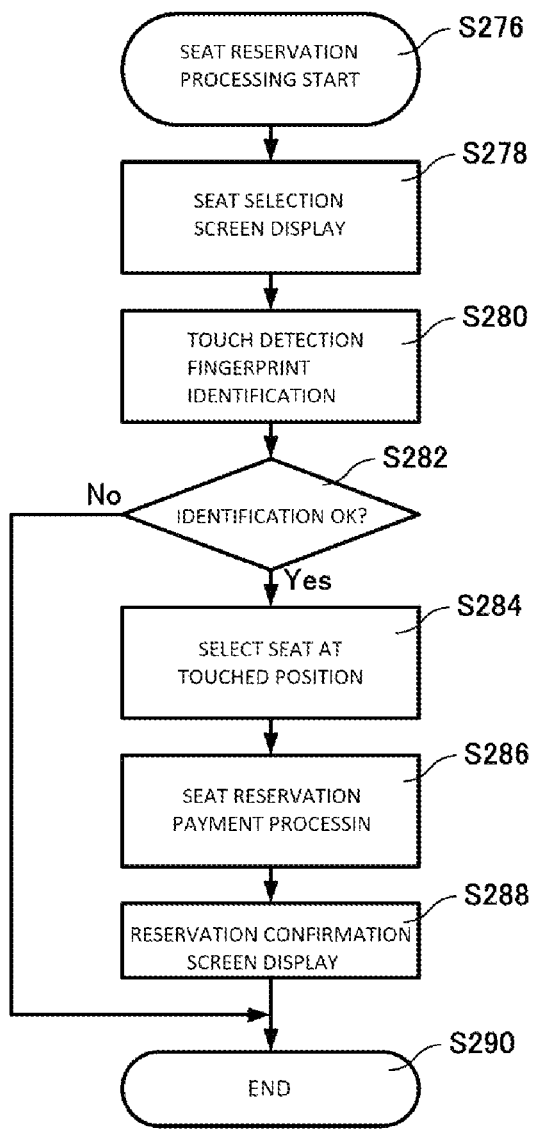
FIG. 18 is a flow chart illustrating processing of the information processing system 200.
Figure 19:
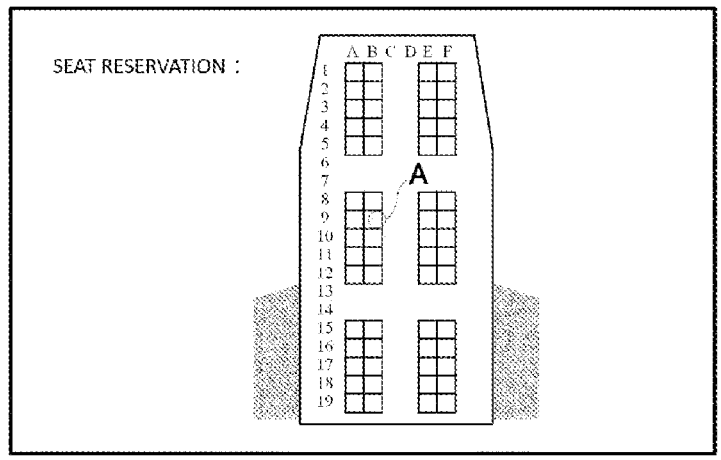
FIG. 19 is a diagram illustrating an example of a display of the information processing system 200.
Figure 20:
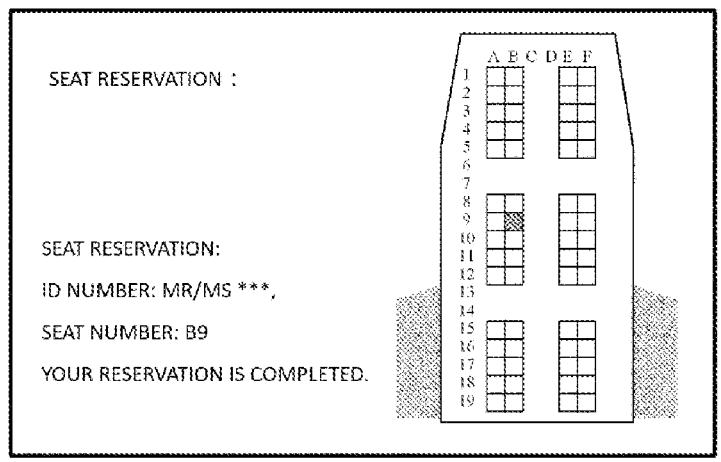
FIG. 20 is a diagram illustrating an example of a display of the information processing system 200.

FIG. 18 is an example of a process flow when the reservation processing is selected. When the reservation processing is started (S276), a seat selection screen is displayed (S278) as illustrated in FIG. 19 and touch detection and fingerprint identification are performed by, for example, contacting a finger to the region A by the user (S280). Whether the identification is passed in the fingerprint identification is determined (S282), and when the identification is passed, a seat "B9" at a touched position is selected (S284) and seat reservation processing and payment processing are performed (S286). As illustrated in FIG. 20, a reservation confirmation screen is then displayed (S288) and the process is terminated (S290). When the identification is determined not to be passed at S282, the process is terminated (S290).

As just described, one operation of contacting a finger (seat selection) by the user simultaneously allows selecting a seat and obtaining image data for passing the personal identification and thus allows the process to be performed without requesting data input and the like of the user for user identification in the payment processing during the seat reservation. As a result, the process flow seen by the user is extremely smooth and it is thus possible to provide good user experience.

As described above, the information processing system 200 in the second embodiment does not require a user to input data for personal identification during access to a personally exclusive file, product purchase, and seat reservation and thus allows smooth progress of a series of process flow in file operation, a reservation site, and an electronic commerce site to achieve excellent user experience.

Although the present invention has been described with reference to the above embodiments, the technical scope of the present invention is not limited to the scope of the above embodiments. It will become apparent to those skilled in the art that the above embodiments may be variously modified or improved. From the appended claims, it will be apparent that the technical scope of the present invention may include such modified or improved embodiments.

For example, although exemplified by a finger of the user in the above embodiments, the position specifier is not limited to this example. In addition, although exemplified by a fingerprint of the user, the body for biometric identification is not limited to this example. For example, it is possible to use, as the biometric information, a pattern or a feature corresponding to a single or a plurality of biometric areas selected from a fingerprint, a vein pattern, the face, an iris, and a voiceprint of the user.

It should be noted that the order of performing each process of the operations, the procedures, the steps, the stages, and the like in the devices, the systems (, programs), and the methods in the appended claims, the description, and the drawings may be achieved in an arbitrary order unless explicitly indicated as "before", "prior to", and the like in particular or unless using an output of previous processing for later processing. Even when the operation flow in the claims, the description, and the drawings is described for convenience using "first", "then", and the like, it does not mean execution in this order is essential.

REFERENCE SIGNS LIST

100 Information Processing System,
110 Input Section,
112 Position Detection Mechanism,
114 Biometric Information Reading Mechanism,
120 Detection Element Formation Region,
120a Detection Element,
120b First Line,
120c Second Line,
122, 124 Vertical Driver Formation Region,
122a, 124a Vertical Driver,
126 Signal Readout Circuit Formation Region,
126a Signal Readout Circuit,
128 Horizontal Coarse Line,
130 Vertical Coarse Line,
132 First Line in Region A,
134 Second Line in Region A,
140 Touch Screen,
150 Imaging Device,
152 Region,
160 Processing Section,
200 Information Processing System,
210 Display Section.

The invention claimed is:

1. An information processing system, comprising:
an input section having a surface and being configured to allow a user to contact or approximate a finger to the surface to input information;
wherein the input section comprises:
a position detection mechanism configured to detect a position of the finger approximate to the surface, and
a reading mechanism configured to read biometric information of the user; and
a processing section configured to perform processing based on the information input to the input section; and
a display section displaying a menu screen,
wherein the input section transmits a position information of a region where a finger contacts to the processing section, and at the same time, the biometric information of the user is transmitted to the processing section, when a menu selection by the user is performed by contacting a screen of the display section with the user's finger,
wherein the reading mechanism and the position detection mechanism comprise a plurality of imaging devices
wherein each of the imaging devices is configured to take an image of a region different from each other on the surface, and
wherein optical resolving of biometric information of the user is performed using only one imaging device, which corresponds to the position of the plurality of the imaging devices.

2. The information processing system according to claim 1, wherein the processing section:
narrows down a region to be read by the reading mechanism based on position information of the finger obtained from the position detection mechanism, and
activates the reading mechanism in the reading region to obtain the biometric information.

3. The information processing system according to claim 1, wherein the processing section is configured to perform next processing based on position information of the finger obtained from the position detection mechanism and attribute information of the user associated with the biometric information obtained from the reading mechanism.

4. The information processing system according to claim 3, wherein the processing section selects and performs, in the next processing, a function in accordance with the attribute information among functions assigned to the position of the display section specified in the position information.

5. The information processing system according to claim 1, wherein the position detection mechanism is a device configured to cause the reading mechanism to function with reduced reading accuracy, a touch screen, or a single or a plurality of imaging devices.

6. The information processing system according to claim 5, wherein the reading mechanism has detection elements arranged in a matrix on the surface, first lines connecting the detection elements in a first direction, and second lines connecting the detection elements in a second direction different from the first direction and is configured to cause the reading mechanism to function as the position detection mechanism by reducing the first lines, the second lines, or both the first lines and the second lines during their function.

7. An information processing system, comprising:
an input section having a surface and being configured to allow a user to contact or approximate a finger to the surface to input information;
wherein the input section comprises:
a position detection mechanism configured to detect a position of the finger approximate to the surface, and
a reading mechanism configured to read biometric information of the user; and
a processing section configured to perform processing based on the information input to the input section; and
a display section displaying a menu screen,
wherein the input section transmits a position information of a region where a finger contacts to the processing section, and at the same time, the biometric information of the user is transmitted to the processing section, when a menu selection by the user is performed by contacting a screen of the display section with the user's finger,
wherein the position detection and reading mechanisms comprise a plurality of imaging devices,
wherein each of the imaging devices is configured to take an image of a distinct, substantially non-overlapping or intersecting region of the input section, and wherein optical resolving of biometric information of the user is performed using only one imaging device, which corresponds to the position, of the plurality of the imaging devices.

8. The information processing system of claim 7, wherein each of the imaging devices is configured to take an image of a distinct, substantially non-overlapping or intersecting region of the input section.

* * * * *